United States Patent
Luther et al.

(10) Patent No.: US 8,886,309 B2
(45) Date of Patent: Nov. 11, 2014

(54) APPARATUS FOR AND METHOD OF TERMINATING A HIGH FREQUENCY ARRHYTHMIC ELECTRIC STATE OF A BIOLOGICAL TISSUE

(71) Applicants: Max-Planck-Gesellschaft zur Foerderung der Wissenschaften e.V., Munich (DE); Cornell University, Ithaca, NY (US)

(72) Inventors: Stefan Luther, Goettingen (DE); Eberhard Bodenschatz, Goettingen (DE); Valentin Krinski, Villeneuve Loubet (FR); Robert Gilmour, Ithaca, NY (US); Flavio H. Fenton, Victor, NY (US)

(73) Assignees: Max-Planck-Gesellschaft zur Foerderung der Wissenschaften E.V., Munich (DE); Cornell University, Ithaca, NY (US)

( * ) Notice: Subject to any disclaimer, the term of this patent is extended or adjusted under 35 U.S.C. 154(b) by 0 days.

(21) Appl. No.: 14/105,243

(22) Filed: Dec. 13, 2013

(65) Prior Publication Data
US 2014/0107721 A1    Apr. 17, 2014

Related U.S. Application Data

(63) Continuation of application No. PCT/EP2012/061377, filed on Jun. 14, 2012.

(60) Provisional application No. 61/497,169, filed on Jun. 15, 2011.

(51) Int. Cl.
*A61N 1/00* (2006.01)
*A61N 1/37* (2006.01)
*A61N 1/362* (2006.01)

(52) U.S. Cl.
CPC ............ *A61N 1/3624* (2013.01); *A61N 1/3702* (2013.01); *A61N 1/3622* (2013.01)
USPC ............................................. 607/14

(58) Field of Classification Search
CPC ... A61N 1/362; A61N 1/3621; A61N 1/3622; A61N 1/3627; A61N 1/365; A61N 1/36592
USPC ............................................. 607/14
See application file for complete search history.

(56) References Cited

U.S. PATENT DOCUMENTS 6,889,077 B2    5/2005    Bornzin et al.
7,418,293 B2    8/2008    Sweeney
(Continued)

FOREIGN PATENT DOCUMENTS

EP    2 177 243 A2    4/2010
WO    2008/035070 A2    3/2008

OTHER PUBLICATIONS

PCT International Search Report and Written Opinion in co-pending, related PCT Application No. PCT/EP2012/061377, mailed Mar. 13, 2013.

(Continued)

*Primary Examiner* — Robert N Wieland
(74) *Attorney, Agent, or Firm* — Thomas | Horstemeyer, LLP

(57) ABSTRACT

For terminating a high frequency arrhythmic electric state of a biological tissue an electric signal representative of the present electric state of the biological tissue is obtained. From the electric signal a dominant frequency of the present electric state is determined, and from the dominant frequency it is determined whether the present electric state of the biological tissue is a high frequency arrhythmic electric state. Further, a dominance level indicative of how dominant the dominant frequency is in the high frequency arrhythmic electric state is determined from the electric signal. Depending on the at least one dominant frequency, at least one series of electric pulses at intervals is generated. The electric pulses are applied to the biological tissue starting at a point in time at which the dominance level exceeds a predefined threshold value for the biological tissue being in a determined high frequency arrhythmic electric state.

56 Claims, 8 Drawing Sheets

(56) References Cited

U.S. PATENT DOCUMENTS

| | | |
|---|---|---|
| 8,265,752 B2 | 9/2012 | Armoundas |
| 8,560,066 B2 | 10/2013 | Efimov et al. |
| 2012/0271368 A1* | 10/2012 | Qu et al. .......................... 607/4 |

OTHER PUBLICATIONS

A. Pumir et al.: "Wave Emission from Heterogeneities Opens a Way to Controlling Chaos in the Heart", (PRL 99, 208101 (2007)).

* cited by examiner a)

b)

a)

b)

a)

b)

APPARATUS FOR AND METHOD OF TERMINATING A HIGH FREQUENCY ARRHYTHMIC ELECTRIC STATE OF A BIOLOGICAL TISSUE

CROSS-REFERENCE TO RELATED APPLICATION

This application is a continuation of PCT Application No. PCT/EP2012/061377, file Jun. 14, 2014, entitled "Apparatus for and Method of Terminating a High Frequency Arrhythmic Electric State of a Biological Tissue", which claims priority to U.S. Provisional Patent Application No. 61/497,169, entitled "Apparatus for and Method of Terminating a High Frequency Arrhythmic Electric State of Biological Tissue". Both of the foregoing applications are incorporated herein by reference in their entireties.

FIELD OF THE INVENTION

The present invention generally relates to an apparatus for and to a method of terminating a high frequency arrhythmic electric state of a biological tissue. In general, the tissue may be any biological tissue. More particular, it is muscle or nerve tissue. Particularly, the biological tissue is heart or brain tissue. Even more particularly, it is a heart or a brain of a living animal which may be a human.

BACKGROUND OF THE INVENTION

In a normal heart, regular waves of electric depolarization of the cellular membrane propagate to trigger the mechanical contractions. Life-threatening arrhythmias of the heart are typically associated with high-frequency rotating electric field waves or spirals. One standard method of terminating arrhythmias, often referred to as defibrillation, is applying a high intensity electric shock to the heart. The high voltage of up to several thousand volt and the resulting currents of some amperes, however, may cause serious damages to the heart and neighboring tissue. Further, defibrillation is painful for the patient which limits the acceptance of implanted defibrillators. Nevertheless, up to now, implanting such defibrillators are the method of choice with patients at risk for life-threatening arrhythmias.

Another established therapy of cardiac arrhythmias is anti-tachycardia pacing (ATP). In ATP the heart is paced faster than its intrinsic rate in the case of ventricular tachycardia. However, ATP fails to terminate high-frequency arrhythmias and fully developed ventricular fibrillation.

Patent application publication US 2006/0100670 A1 proposes cardiac stimulation methods and systems that provide for multiple pulse defibrillation. These methods and systems involve sensing a fibrillation event, determining a fibrillation cycle length associated with the fibrillation event, and delivering a plurality of defibrillation pulses to treat the fibrillation event. The defibrillation pulses are delivered using a combination of subcutaneous and non-intrathoracic electrodes. Delivery of each defibrillation waveform subsequent to a first defibrillation waveform is separated in time by a delay associated with the fibrillation cycle length. Particularly, delays between defibrillation waveform delivery are associated with a percentage of the fibrillation cycle length. The actual number of defibrillation pulses delivered in the embodiments of US 2006/0100670 A1 is 2 or 3, particularly 2. The actual delay between the individual pulses is between about 50% and about 125% of the average cycle length and typically it is between about 75% and about 100% of the average cycle length, where the cardiac response to multiple separated pulses is similar to the cardiac response to a single pulse. This region, which is considered as similar to a region of constructive interference for the cardiac response to the separated response to the separated pulses, is told to provide opportunities for improved efficacy of defibrillation and/or decreased energy requirements for defibrillation systems.

A. Pumir et al.: "Wave Emission from Heterogeneities Opens a Way to Controlling Chaos in the Heart" (PRL 99, 208101 (2007)) suggest to use wave emission from heterogeneities (WEH) induced by periodic pulses of an electric field as a method of chaos control of waves in the heart. This method is said to be more effective than ATP and to require much less energy than the defibrillating shock. Particularly, the single pulses are of such a low electric field that they do not terminate a rotating wave, but the train of pulses applied in WEH can.

There is still a need for an easily workable regime of terminating a high frequency arrhythmic electric state of a biological tissue with low electric field pulses causing as little tissue damage and pain as possible.

SUMMARY OF THE INVENTION

The present invention relates to an apparatus for terminating a high frequency arrhythmic electric state of a biological tissue, the apparatus comprising: at least one sensor for providing an electric signal representative of the present electric state of the biological tissue; a determination unit which determines from the electric signal at least one dominant frequency of the present electric state of the biological tissue, and which determines from the at least one dominant frequency whether the present electric state of the biological tissue is a high frequency arrhythmic electric state; an electric pulse generator for generating at least one series of electric pulses at intervals depending on the at least one dominant frequency; and at least one electrode connected to the pulse generator for applying the electric pulses to the biological tissue. For terminating a determined high frequency arrhythmic electric state of the biological tissue, the determination unit determines from the electric signal a dominance level indicative of how dominant the at least one dominant frequency is in the high frequency arrhythmic electric state; and triggers the electric pulse generator to generate the at least one series of electric pulses starting at a point in time at which the dominance level determined exceeds a predefined threshold value.

In another aspect, the present invention relates to a method of terminating a high frequency arrhythmic electric state of a biological tissue, the method comprising: obtaining a electric signal representative of the present electric state of the biological tissue; determining from the electric signal at least one dominant frequency of the present electric state of the biological tissue; determining from the at least one dominant frequency whether the present electric state of the biological tissue is a high frequency arrhythmic electric state; determining from the electric signal a dominance level indicative of how dominant the at least one dominant frequency is in the high frequency arrhythmic electric state; generating at least one series of electric pulses at intervals depending on the at least one dominant frequency; and applying the electric pulses to the biological tissue starting at a point in time at which the dominance level exceeds a predefined threshold value for the biological tissue being in a determined high frequency arrhythmic electric state.

In another aspect, the present invention relates to an apparatus for terminating an atrial fibrillation of an atrium of a heart, the apparatus comprising: at least one sensor configured to provide an electric signal representative of the present electric state of the atrium; a determination unit configured to determine from the electrical signal whether the present electric state of the biological tissue is an atrial fibrillation; an electric pulse generator for generating at least one series of electric low energy anti-fibrillation pacing pulses at intervals depending on the electrical signal; at least one electrode connected to the pulse generator configured to apply the low energy anti-fibrillation pacing pulses to the atrium; at least one further sensor configured to provide a further electric signal representative of an ventricular action potential of a ventricle of the heart; a further electric pulse generator configured to generate electric pacing pulses; at least one further electrode connected to the further pulse generator and configured to apply the electric pacing pulses to the ventricle; and a synchronization unit configured to synchronize the at least one series of low energy anti-fibrillation pacing pulses with the electric pacing pulses such that no low energy anti-fibrillation pacing pulse of the at least one series of low energy anti-fibrillation pacing pulses is applied in a vulnerable window during which the ventricle is susceptible to shock-induced ventricular fibrillation.

In yet another aspect, the present invention relates to a method of terminating an atrial fibrillation of an atrium of a heart, the method comprising: obtaining a electric signal representative of the present electric state of the atrium; determining from the electric signal whether the present electric state of the biological tissue is an atrial fibrillation; generating at least one series of electric low energy anti-fibrillation pacing pulses at intervals depending on the electric signal; obtaining a further electric signal representative of an ventricular action potential of a ventricle of the heart; generating electric pacing pulses; applying the electric pacing pulses to the ventricle; generating at least one series of electric low energy anti-fibrillation pacing pulses at intervals depending on the electric signal; applying the low energy anti-fibrillation pacing pulses to the atrium; and synchronizing the at least one series of low energy anti-fibrillation pacing pulses with the electric pacing pulses such that no low energy anti-fibrillation pacing pulse of the at least one series of low energy anti-fibrillation pacing pulses is applied in a vulnerable window during which the ventricle is susceptible to shock-induced ventricular fibrillation.

Other features and advantages of the present invention will become apparent to one with skill in the art upon examination of the following drawings and the detailed description. It is intended that all such additional features and advantages be included herein within the scope of the present invention, as defined by the claims.

BRIEF DESCRIPTION OF THE DRAWINGS

The invention can be better understood with reference to the following drawings. The components in the drawings are not necessarily to scale, emphasis instead being placed upon clearly illustrating the principles of the present invention. In the drawings, like reference numerals designate corresponding parts throughout the several views.

DETAILED DESCRIPTION

Figure 1:
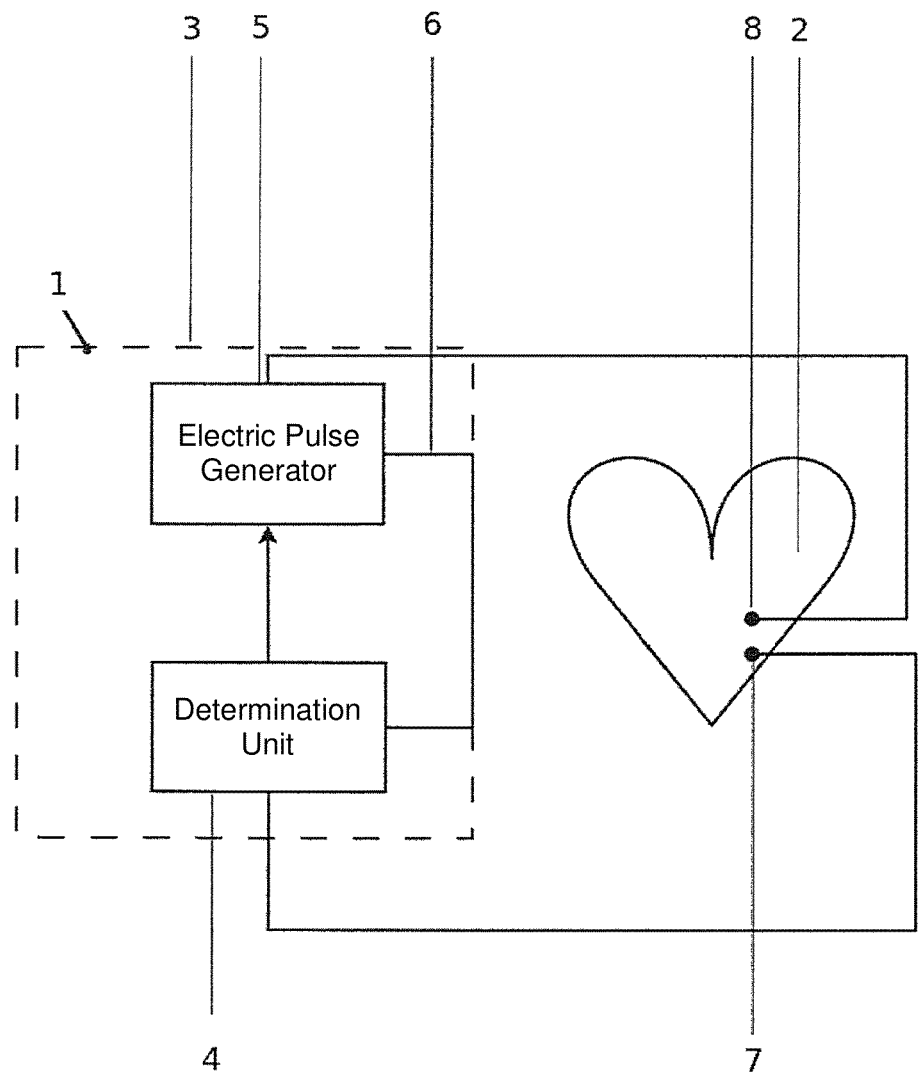
FIG. 1 illustrates a basic setup of an apparatus for terminating a high frequency arrhythmic electric state of a biological tissue.

In order to determine a high frequency arrhythmic electric state of a biological tissue the electric state of the biological tissue has to be captured at least with regard to a dominant frequency of the high frequency arrhythmic electric state. This will typically be achieved using a sensor sensing the electric state of the biological tissue which provides an electric signal representative of the electric state of the biological tissue, and using a determination unit determining the dominant frequency from the electric signal.

From the determined dominant frequency of the present electric state, the determination unit can then determine whether the present electric state is a high frequency arrhythmic electric state of the biological tissue. If a high frequency arrhythmic electric state is determined, at least one series of electric pulses is applied to the biological tissue. An electric pulse generator is provided for generating the at least one series of electric pulses at intervals depending on the at least one dominant frequency; and at least one electrode connected to the pulse generator is provided for applying the electric pulses to the biological tissue.

The inventors noticed that similar arrhythmic electric states of a same biological tissue will sometimes be completely terminated and sometimes not at all be terminated by same series of electric pulses. Further, they found that the success in terminating the arrhythmic electric state is not a simple matter of probability, but that the electric chaos ruling the arrhythmic electric state of the biological tissue does not display a uniform level of disorganization over the time, but that there is a continual coming and going of aspects of electric field coordination between different areas of the biological tissue. The total of this coordination shows a fluctuation with significant maxima. If the series of electric pulses is applied to the biological tissue at a point in time at which such a maximum coordination is reached, the probability of terminating the high frequency arrhythmic electric state of the biological tissue is quite high, whereas it is quite low if the series of electric pulses is applied to the biological tissue in a minimum between two of these maxima. According to the interpretation of the inventors, which should however not be taken as a limitation to the present invention, the series of electric pulses starting at one of the maxima only has to provide for some more electric field coordination in the biological tissue to terminate the high frequency arrhythmic electric state, whereas, if applied in a minimum, the series of electric pulses has to start from zero in electrically coordinating the biological tissue.

The inventors also found that the present total electric field coordination within the biological tissue being in a high frequency arrhythmic electric state can be assessed in that it is determined how dominant the dominant frequency is in the high frequency arrhythmic electric state, a strong dominance of the dominant frequency indicating a high total electric field coordination within the biological tissue. Particularly, the determination unit may determine from the electric signal representative of the present electric state of the biological tissue a dominance level indicative of how dominant the at least one dominant frequency is in the high frequency arrhythmic electric state, and trigger the electric pulse generator to generate the at least one series of electric pulses starting at a point in time at which the dominance level exceeds a predefined threshold value.

In this way, the series of electric pulses is applied to the biological tissue at an optimum point in time with regard to the probability of terminating the high frequency arrhythmic electric state. This also means that the voltage and energy of the electric pulses applied at this optimum point in time may be lower than the voltage and energy of a series of electric pulses applied at any other point in time, even if the same probability of terminating the high frequency arrhythmic electric state is to be achieved. Thus, the method of the present invention is named Low Energy Antifibrillation Pacing (LEAP).

The predefined threshold value used for defining the optimum point in time for applying the series of electric pulses to the biological tissue may be adjusted to the maxima of electric coordination typically occurring within a particular biological tissue within any of its high frequency arrhythmic electric states.

Particularly, the threshold value may be a percentage of a previously recorded maximum value of the dominance level. In this way, the threshold value is automatically adapted to the maximum dominance levels presently occurring in the present high frequency arrhythmic electric state. The percentage of the previously recorded maximum value of the dominance level may be adjusted to a suitable value within a typical range of 80% to 95%, like for example to 90%.

In determining the dominance level, the determination unit may filter the electric signal for frequency components in a frequency range extending on at least one side of the dominant frequency. Preferably, the frequency range for which the determination unit filters extends on both sides of the dominant frequency. Particularly, it may stretch from about a half of the dominant frequency to twice of the dominant frequency. The concentration of the intensity of the electric signal within this frequency range on the dominant frequency is a very well suited criterion for assessing the electric coordination of the biological tissue being in a high frequency arrhythmic electric state.

For determining the dominance level, the determination unit may compare the intensity of the electric signal at the dominant frequency with the intensity of the electric signal at least one neighboring frequency. The ratio of these intensities may be taken as the dominance level. Particularly, the intensity of the electric signal at the dominant frequency may be compared with the intensity of the electric signal at least one neighboring frequency in that an integral of the intensities of the electric signal within a frequency window including the dominant frequency and an integral of the intensities of the electric signal within a frequency window including the neighboring frequency are compared. Using such frequency windows will also have a smoothing effect on the dominance level in that noise is reduced by which the dominance level determined may be affected. Such a comparison between the intensity of the electric signal at two different frequencies is easily accomplished in or close to real time.

The inventors also noticed that different biological tissues even of the same kind show quite different electric propagation properties relevant in terminating a high frequency arrhythmic electric state of the biological tissue by applying a series of electric pulses. Particularly, these different electric propagation properties require different voltages or energies of the electric pulses to achieve a certain probability of terminating the high frequency arrhythmic electric state with one series of electric pulses. Thus, reaching a suitable probability of terminating the high frequency arrhythmic electric state with pulses of low voltage and energy requires assessing the actual electric properties of the biological tissue. However, it is unsuitable to make this assessment by a simply trial and error procedure in which electric pulses of different voltage and electric energy are applied to the biological tissue previously voluntarily transferred into a high frequency arrhythmic electric state. The inventors found that the electric propagation properties of a biological tissue may be suitably assessed starting from a non-electrically excited base state of the biological tissue. In a beating heart, for example, such a non-electrically excited base state is present between the individual heartbeats. If, in this electric base state of the biological tissue, individual electric pulses of a same duration but of different voltages are applied to the biological tissue and if electric signals sensed at the biological tissue after each individual electric pulse, i.e. in response to the individual electric pulse, are evaluated, the electric properties of the biological tissue can be estimated for adjusting a minimum suitable voltage of the electric pulses of the at least one series of electric pulses to be generated by the electric pulse generator for successfully terminating a future high frequency arrhythmic electric state of the biological tissue. The dependence of the response, particularly of the response time of the biological tissue to an individual electric pulse on the voltage or electric field of the electric pulses applied may be evaluated as a power law. This power law allows for conclusions on the distributions of heterogeneities in the biological tissue from which wave emissions may be induced by the electric pulses of the series of electric pulses.

This assessment of the electric properties of the biological tissue may be carried out in a set up mode of an apparatus for determining a high frequency arrhythmic electric state of the biological tissue in which the electric pulse generator generates the individual electric pulses at the same duration and at the different voltage taken from the same ranges and voltages which may be suitable for the electric pulses of the series of electric pulses to be generated by the electric pulse generator for terminating a future high frequency arrhythmic electric state of the biological tissue.

The dominant frequency of the high frequency arrhythmic electric states also defines a phase space of all potential phasings of electric waves of that dominant frequency in the biological tissue. The phase space defined by the dominant frequency corresponds to a duration in the ordinary time space which is equal to the reciprocal value of the dominant frequency or to its periodic time. To the end of terminating the high frequency arrhythmic electric state of the biological tissue, a series of electric pulses is applied to the biological tissue which raster scan the full phase space defined by the dominant frequency once. It is to be noted that both raster scanning the full phase space and only scanning it once are relevant aspects of some embodiments of the apparatus and method of the present invention. Scanning it once ensures hitting each rotating wave contributing to the high frequency arrhythmic electric state of the biological tissue in a vulnerable window of its phasing. Scanning the full phase space not more than once avoids creating a secondary high frequency arrhythmic electric state in the biological tissue with the electric pulses applied. As raster scanning the phase space means that every circular wave to be terminated is subjected to an electric pulse in its vulnerable window, the electric energy of each electric pulse can be kept low without losing the necessary efficacy within the vulnerable window. This low electric energy of the single electric pulses also reduces the danger of creating a secondary unwanted electric state of the biological tissue, as the electric energy may simply be to low for this.

Whereas each series of electric pulses only raster scans the full phase space defined by the dominant frequency once, more than one series of electric pulses may be applied to the biological tissue to terminate the high frequency arrhythmic electric state at intervals which are much longer than the intervals at which the electric pulses of one series follow each other. Preferably, the intervals of the series are even longer than the duration of each single series of electric pulses.

The time intervals at which the single electric pulses of each series of electric pulses are generated have to be selected such that the phase space defined by the at least one dominant frequency is raster scanned at sufficiently small phase intervals to hit every rotary wave in its vulnerable window but with as low a total number of electric pulses as possible.

Typically, the phase space should be raster scanned at phase intervals in a range from $\pi/16$ to $2\pi/5$, $2\pi$ been the dimensionless size of the phase space. Preferably, the phase space is scanned at phase intervals in a range from $\pi/5$ to $2\pi/7$ which means that about 7 to 10 individual pulses at equal intervals are needed to raster scan the full phase space once. Generally, the intervals of the individual pulses do not need to be equal. They may even be non-equal on purpose to avoid the excitation of any periodic electric states of the biological tissue. However, they may be equal or at least about equal to uniformly raster scan the phase space.

Actually, the electric pulses may be generated at time intervals deviating from the reciprocal value of the dominant frequency by a deviation in time in a range of 1/32 to 1/5, preferably from 1/10 to 1/7 of the reciprocal value of the dominant frequency.

Generally, the electric pulses may be generated at intervals being smaller than the reciprocal value of the dominant frequency. Preferably, however, the intervals of the electric pulses exceed the reciprocal value by the deviation in time discussed above.

The time intervals and the phase intervals of the electric pulses discussed above include the pulse duration of the electric pulses of the series of electric pulses. This pulse duration should be selected to apply sufficient electric energy within the vulnerable window of the rotating waves to be terminated at the electric field strength applied. On the other hand, this electric energy and thus the pulse duration should be kept low. Actually, the duration per pulse is in a typical range of 2 to 25 ms. Preferably, it is in a range from 5 to 15 ms.

The electric field to be applied across the biological tissue in each individual pulse which is necessary to terminate the rotating waves in their vulnerable window may be as low as 0.05 Volt/cm. 3 Volt/cm may be regarded as an upper limit for the electric field strength suitably applied for terminating a high frequency arrhythmic state of a biological tissue. The preferred range of the field strength is from 0.1 to 1 Volt/cm.

As compared to a standard heart defibrillation energy, the electric pulses of the series of electric pulses may be in a typical range from only 1/400 to 1/2 at maximum. Preferably, the electric energy per pulse is in a range from 1/200 to 1/5, even more preferably it is in a range from 1/100 to 1/10 of the standard heart defibrillation energy. Even if the total electric energy applied to the biological tissue over one full series of pulses equals the standard heart defibrillation energy which is known to those skilled in the art, the potential damage to the biological tissue is much lower as the energy is distributed over a longer period of time, and as the maximum currents flowing through the biological tissue are, thus, much smaller.

The electric energy per pulse may even be reduced further, if a plurality of series of electric pulses is generated, and if the single series of electric pulses are applied to different electrodes to successively create electric fields across the biological tissue in different spatial directions. This aspect accounts for the fact that rotating waves making up a high frequency arrhythmic electric state of a biological tissue not only differ in their phasing but also in their spatial orientation. Thus, they do not only have a vulnerable window in the phase space but also in the three dimensional space. If this vulnerable window in the three dimensional space and in the phase space can be met in the same time, a particularly low electric energy it sufficient to terminate the respective rotating wave.

To the end of only applying as low a number of electric pulses to the biological tissue as necessary, it may be determined from the electric signal which is representative of the electric state of the biological tissue whether the biological tissue is still in the arrhythmic electric state after each series of the electric pulses applied. Only if the biological tissue is still in the arrhythmic electric state, a further series of electric pulses may be applied to the biological tissue.

According to the present invention, the voltage and energy of the electric pulses of the series of the electric pulses applied to terminate a high frequency arrhythmic electric state of the biological tissue are kept as low as possible. Due to the measures described here, the voltage and energy of the pulses is nevertheless suitable for achieving a high probability of the desired termination with a single series of the electric pulses. Nevertheless, there is little use in applying a high number of such series and staying with the same voltage and energy of the electric pulses. Instead, at least one further series of electric pulses may be generated at a higher voltage than a previous series of electric pulses, to increase the probability of terminating the high frequency arrhythmic electric state of the biological tissue quickly. Damage to the biological tissue and pain to a patient comprising the biological tissue may increase with the increasing voltage of the electric pulses. However, there is a good justification for this, if the arrhythmic electric state can not be terminated with low voltages.

Further, if it has to be noticed that, even after a number of series of electric pulses with increasing voltage, the biological tissue is still in the arrhythmic electric state, a single electric pulse of a standard heart defibrillation energy may be generated and applied to the biological tissue. This means that, if the arrhythmic electric state cannot be terminated by series of electric pulses of low voltage and energy which only cause little to no damage and pain, a standard defibrillation technique may be applied to ultimately terminate the arrhythmic electric state, which may otherwise be fatal to the biological tissue and the entire organism comprising the biological tissue.

A criterion for the biological material being in a high frequency arrhythmic electric state is the dominant frequency of the electric signal representing the electric state of the biological tissue. A high frequency arrhythmic electric state is characterized by a frequency in a range from about 5 to about 20 Hertz.

If there is more than one dominant frequency in the electric signal representative of the electric state of the biological tissue, the highest dominant frequency of the electric signal may be taken as the dominant frequency defining the phase space to be scanned by the electric pulses.

The electric pulses may be applied between at least one electrode and a housing of an electric pulse generator forming a counter electrode. This housing may also include the further parts of the apparatus for terminating a high frequency arrhythmic electric state of a biological tissue.

The electrode connected to the pulse generator, on the other hand, may be a cardiac electrode. Particularly, it may be an intrathoracic electrode. In another variant, it may be a brain electrode, particularly a non-intracerebral electrode.

In a further variant it may be a skeletal muscle electrode, particularly a non-subcutaneous electrode.

In one embodiment, the method of anti-fibrillation pacing disclosed here is applied to suppress atrial fibrillation (AF) by delivering low energy anti-fibrillation pacing (LEAP) pulses to the fibrillating atrium. As with other electrical therapies that have been devised to suppress AF, the LEAP shocks must be applied outside of the ventricular "vulnerable window" to avoid shock-induced induction of ventricular fibrillation (VF) by the far-field LEAP pulses, i.e., the far-field pulses have to be prevented from being applied to the atria during the vulnerable period of the ventricle to prevent the possible induction of VF. Note that the ventricular vulnerable window is not the vulnerable window of the rotating waves. Whereas a suitable pulse applied during the vulnerable window of a rotating wave will terminate the rotating wave, a pulse applied during the vulnerable window of the ventricle may cause VF.

Because ventricular activation during AF typically is irregular, sensing of ventricular activity and synchronization of, for example, 5 far-field pulses can be problematic. To overcome this obstacle, the present invention teaches to pace the ventricle at a constant cycle length prior to the delivery of the LEAP, as well as during the LEAP, to capture and regularize a defined ventricular rhythm. The pacing stimuli may be delivered using an indwelling pacing/sensing catheter placed in the apex of the right ventricle and unipolar recordings may be obtained from the catheter. The activation recovery interval (ARI), as measured from the right ventricular unipolar electrogram prior to LEAP, will be used by a controller that synchronizes the delivery of LEAP so that no LEAP pulses are delivered during the vulnerable windows of the ventricle. The controller may be imbedded in the same ICD-like device that houses the LEAP algorithms.

In other embodiments of LEAP, LEAP protocols are applied that are effective at energies below the ventricular excitation threshold during the ventricular relative refractory period (i.e., the vulnerable window). Consequently, a ventricular pacing/sensing catheter is not required here.

Referring now in greater details to the drawings, FIG. 1 illustrates the basic design of an apparatus 1 for terminating a high frequency arrhythmic electric state of a biological tissue 2. In a housing 3 indicated by a dashed line the apparatus 1 comprises a determination unit 4 and an electric pulse generator 5. Both the determination unit 4 and the electric pulse generator 5 are connected to a counter electrode 6 forming part of the housing 3. The counter electrode 6 serves as a counter electrode to an electrode 7 of the determination unit 4, which serves as a sensor providing an electric signal representative of the electric state of the biological tissue 2. The determination unit 4 determines any dominant frequency of the electric state of the biological tissue 2 and selects the highest dominant frequency. If this highest dominant frequency is indicative of a high frequency arrhythmic electric state of the biological tissue 2, the determination unit activates the electric pulse generator 5 to generate at least one series of electric pulses depending on the determined dominant frequency. These electric pulses are applied to the biological tissue 2 between the counter electrodes 6 and an electrode 8 to terminate the high frequency arrhythmic electric state of the biological tissue 2.

Figure 2:
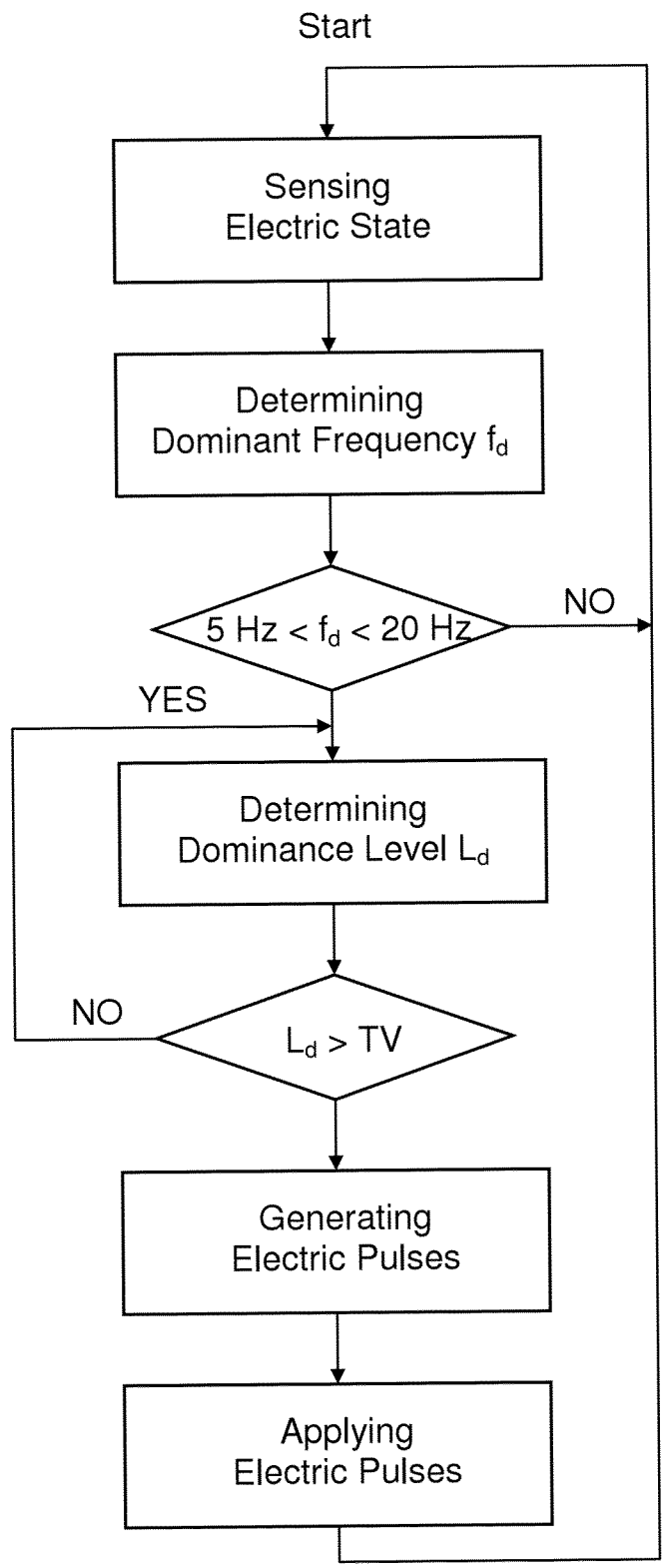
FIG. 2 is a block diagram of a method of terminating a high frequency arrhythmic electric state of a biological tissue applying electric pulses to the biological tissue using the apparatus according to FIG. 1.

FIG. 2 is a simplified block diagram indicative on the method executed when using the apparatus 1 according to FIG. 1. In a first step, the electric state of the biological tissue is sensed with a sensor providing an electric signal. The electric signal representative of the electric state is then analyzed with regard to at least one dominant frequency of the electric state. If this dominant frequency is a characteristic range from 5 Hertz to 20 Hertz, a dominance level of the dominant frequency is also determined. Beginning at a point in time at which the dominant frequency is above a threshold value TS, electric pulses are generated depending on the dominant frequency. These electric pulses are then applied to the biological tissue. Afterwards, the electric state of the biological tissue is sensed again as it is done, if the dominant frequency is not in the characteristic range.

Figure 3:
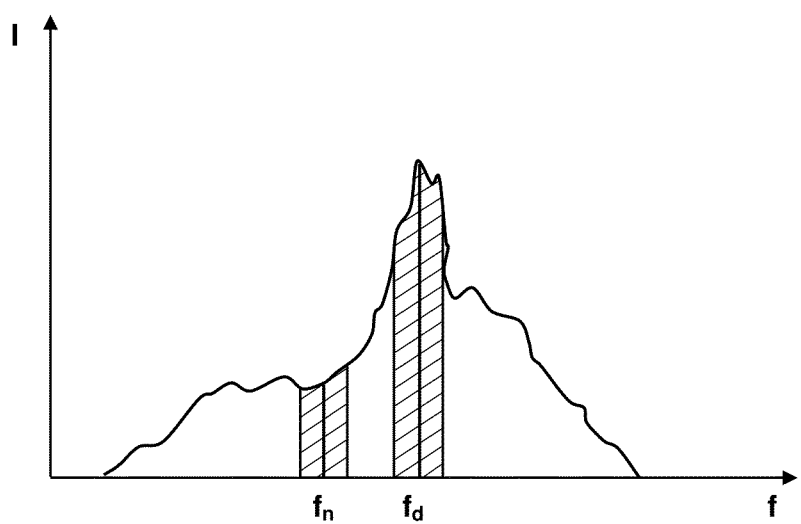
FIG. 3 illustrates a concept of determining an optimum starting point for applying the electric pulses to the biological tissue in the method according to FIG. 2.
Figure 3:
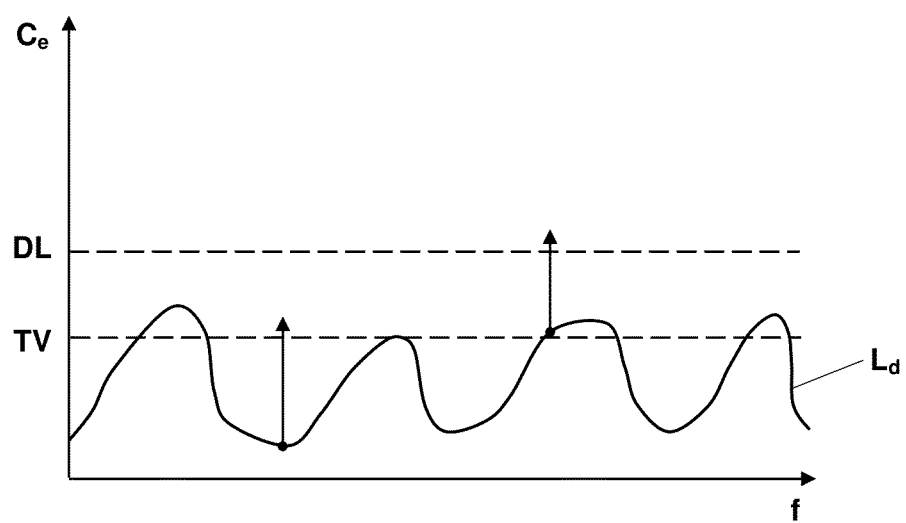

FIG. 3 (a) shows a typical intensity distribution of an electric signal representative of the present electric state of a biological tissue plotted over its frequency, if the biological tissue is in a high frequency arrhythmic electric state. The intensity I is highest at a dominant frequency $f_d$ but there are also other frequencies of considerable intensity. The concentration of the intensity I on the dominant frequency $f_d$ fluctuates over time. The dominance level $L_d$ of the dominant frequency $f_d$ may be measured in that the integral of the intensity I over a frequency window including the dominant frequency $f_d$ is compared to an integral of the intensity I over a frequency window including a neighboring frequency $f_n$ adjacent to the dominant frequency $f_d$. FIG. 3 (b) is a plot of the electric field coordination $C_e$ of the various areas of a biological tissue being in an arrhythmic electric state over the time t. The dominance level $L_d$ is a measure of this electric coordination $C_e$ in the arrhythmic electric state. FIG. 3 (b) shows that the dominance level $L_d$ fluctuates over time and shows maxima at a distance in time in the order of seconds. Arrows of same vertical lengths indicate a possible increase in electric coordination of the biological tissue caused by a series of electric pulses applied to the biological tissue. If this series of electric pulses is applied when the dominance level is only low, the resulting overall electric coordination will not exceed a determination level DL above which the electric field coordination of the biological tissue is so high that the arrhythmic electric state is terminated. If, however, the series of electric pulses is applied at a point in time at which the dominance level $L_d$ already is above the threshold value TV, the resulting overall electric field coordination becomes higher than the determination level DL. Thus, determining the dominance level $L_d$ and triggering the series of electric pulses when the dominance level $L_d$ exceeds the threshold value TV strongly enhances the chances to terminate the arrhythmic electric state of the biological tissue with a single series of electric pulses of a certain voltage and energy.

Figure 8:
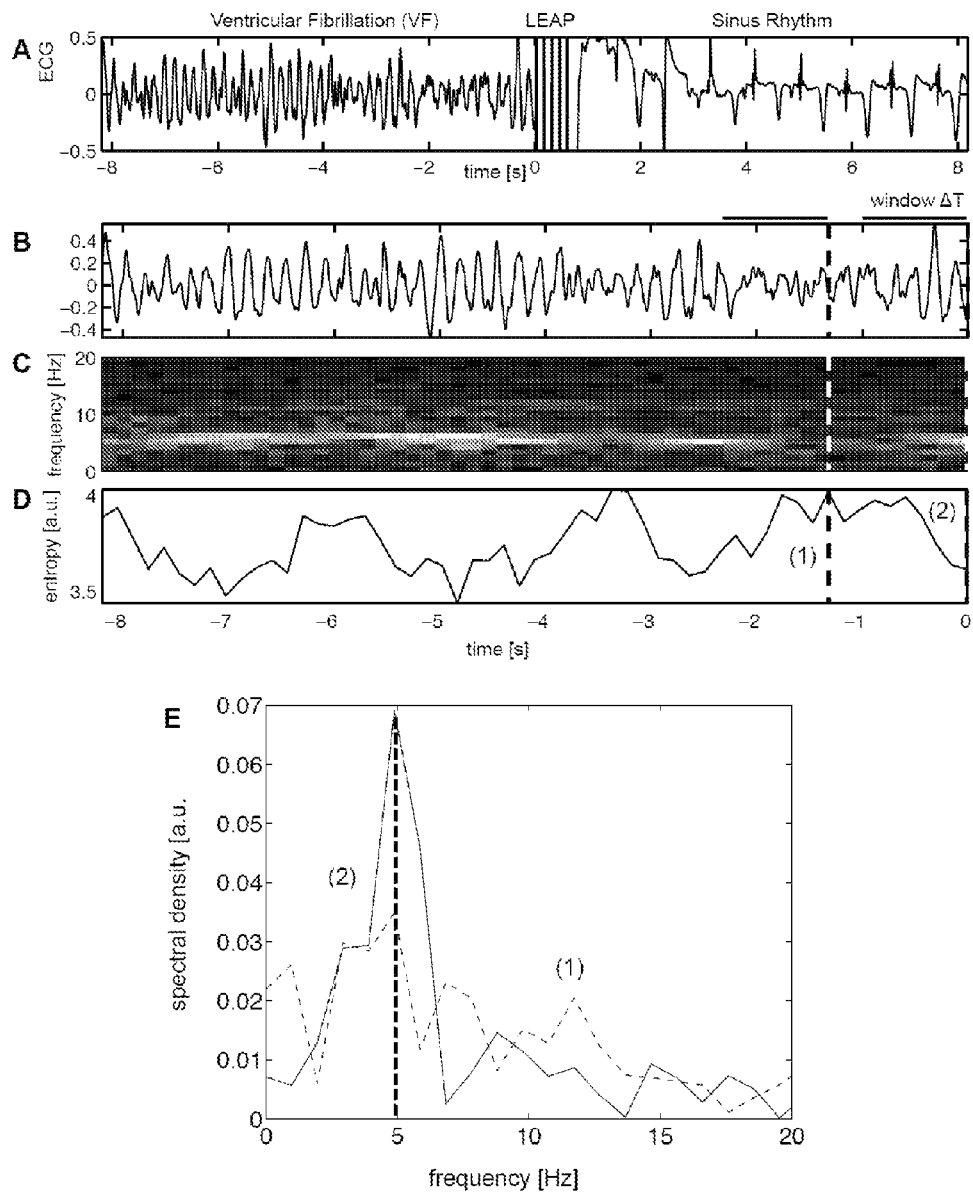
FIG. 8 illustrates a more detailed illustrates a concept of determining an optimum starting point for applying the electric pulses to the biological tissue in the method according to FIG. 2.

FIG. 8 A depicts a time series of an electrocardiogram (ECG) showing successful termination of ventricular fibrillation in vivo at t=0 using low energy anti-fibrillation pacing (LEAP) pulses (N=5 pulses, pacing frequency 6.5 Hz). FIG. 8 B represents the interval of the time series shown in A preceding the LEAP pulses. Black bars indicate time intervals ΔT, which were used to obtain spectra shown in FIG. 8 C. FIG. 8 C is a spectrogram of the time series shown in FIG. 8 B indicating temporal fluctuations of the spectral content of the signal. Each spectrum was computed using Fast Fourier Transform and a time window of a length ΔT. FIG. 8 D depicts a spectral entropy obtained from the spectrogram and displays corresponding fluctuations of the spectral complexity as observed in FIG. 8 C. FIG. 8 E shows two representative spectra obtained at times (1) (plotted with a solid line in FIG. 8 D) and (2) (plotted with a dashed line in FIG. 8 D) as indicated in FIGS. 8 B-D with dashed vertical lines.

The sprectral entropy depicted in FIG. 8 D is defined as follows:

$$e = -\frac{1}{\ln(N)} \sum_{i=1}^{N} p_i \ln(p_i),$$

wherein N is the total number of spectral bins, and $p_i$ is a normalized power spectral density in the i-th spectral bin.

Figure 4:
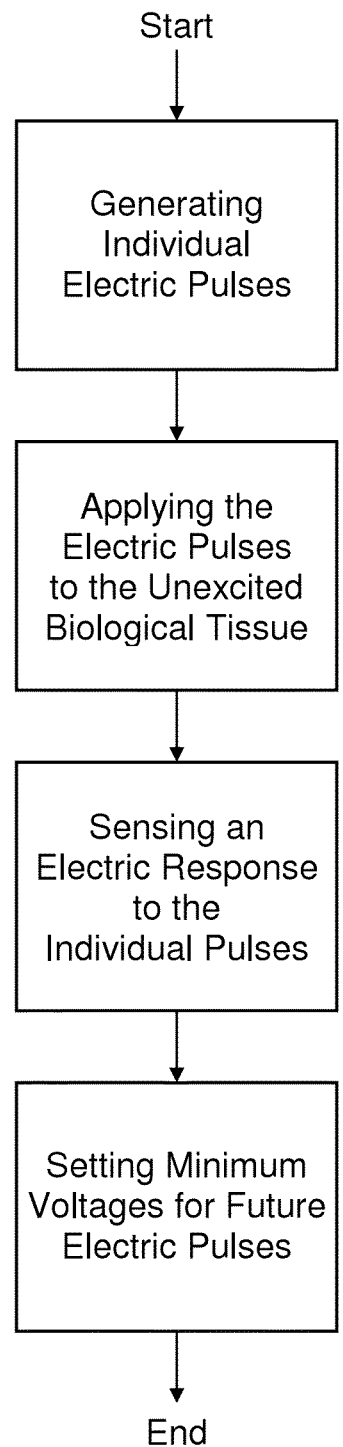
FIG. 4 illustrates a concept of determining a minimum suitable voltage of the electric pulses to be applied in the method according to FIG. 2.

FIG. 4 is a simplified block diagram of a set up procedure of the apparatus shown in FIG. 1. This set up procedure is only carried out when the biological tissue is not in an electrically excited state. Such an unexcited electric state of the biological tissue, however, is also present between the individual heartbeats of a beating heart, for example.

To this unexcited biological tissue individual electric pulses of a same duration but of different voltages are applied, and an electric response to the individual pulses, particularly a response time within which a certain electric potential is reached at a point distant to an electrode by which the individual electric pulsed are applied, is sensed. The dependency of these response times on the voltage of the individual electric pulses is then used to draw conclusions regarding the electric field propagation properties of the biological tissues and to set minimum voltages for suitable electric pulses of series of electric pulses to be applied to the biological tissue in future events of high frequency arrhythmic electric states. With a heart defibrillation apparatus, the procedure according to FIG. 4 may only be carried out under medical surveillance when implanting and setting up the defibrillation apparatus. With low voltage individual pulses it may, however, also be carried out at certain intervals of time to update the minimum voltages for the electric pulses of the series of electric pulses to compensate for any changes in the electric propagation properties of the biological tissue.

Figure 5:
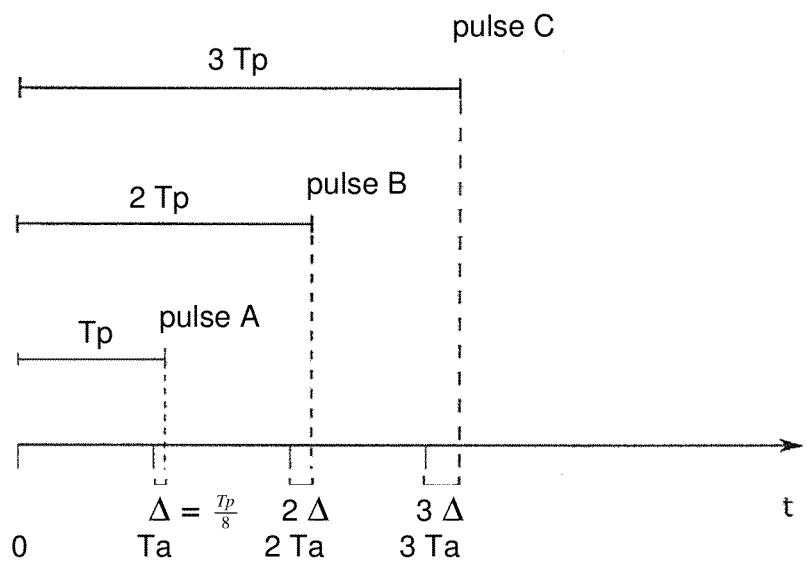
FIG. 5 illustrates a concept of raster scanning the phase space of a dominant frequency of the arrhythmic electrical state in the method according to FIG. 2.
Figure 5:
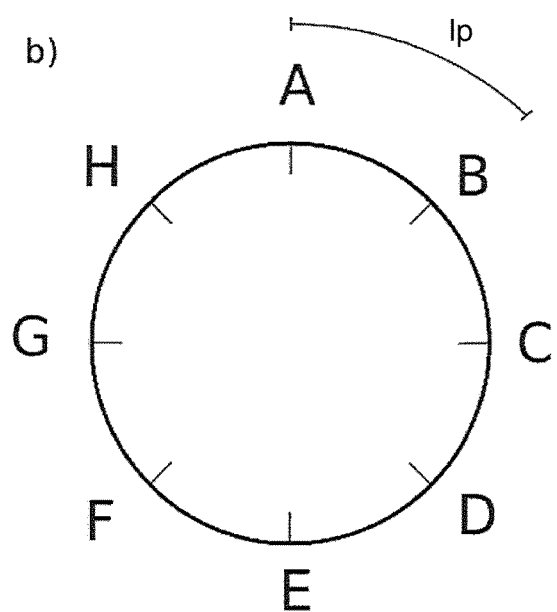

FIG. 5 shows, how a series of electric pulses A to H is generated depending on the reciprocal value 1/f of the dominant frequency f. The intervals Tp of the individual pulses A to H exceed the reciprocal value 1/f by a deviation Δ which is ⅛ of the reciprocal value 1/f. FIG. 5 (a) shows the pulses in the time space, whereas FIG. 5 (b) depicts the pulses A to H in the phase space, where they raster scan the full phase space of $2\pi$ at the dominant frequency exactly once at intervals $I_P$ of $\pi/4$. Any rotating wave of the dominant frequency f has a vulnerable window in the phase space which is hit by one of the pulses A to H according to FIG. 5 (b).

Figure 6:
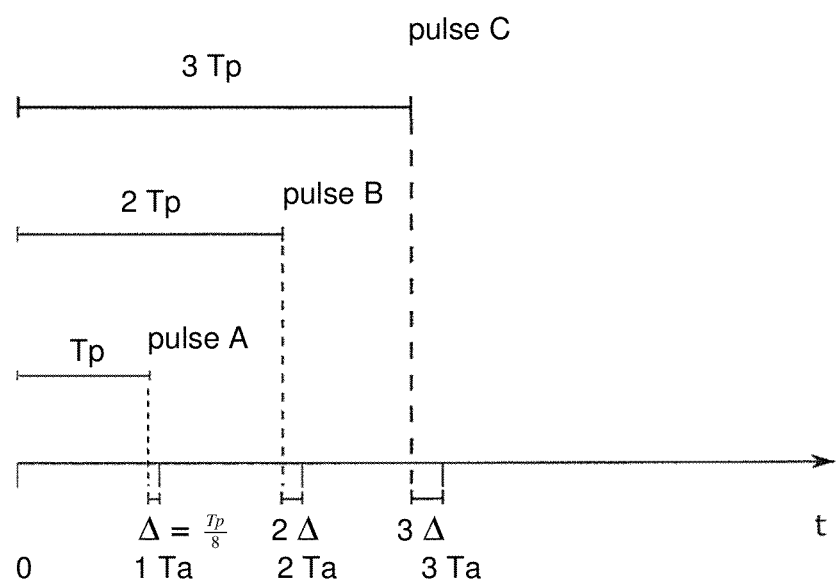
FIG. 6 illustrates another concept of raster scanning the phase space of a dominant frequency of the arrhythmic electrical state in the method according to FIG. 2.
Figure 6:
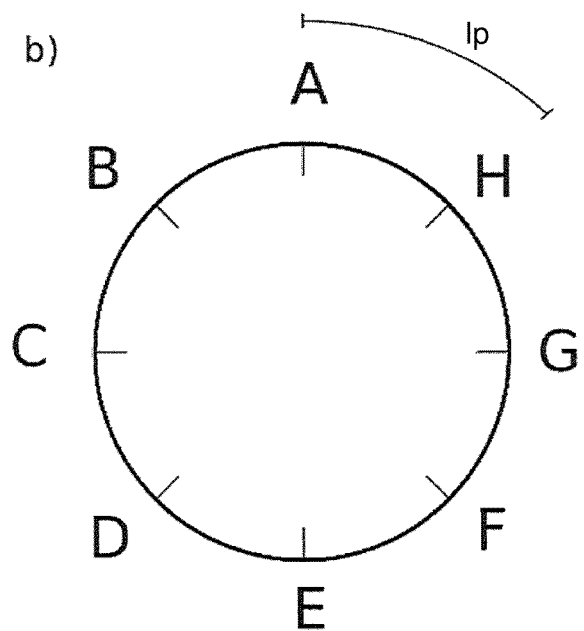

FIG. 6 shows, how another series of electric pulses A to H is generated depending on the reciprocal value 1/f of the dominant frequency f. Here, the intervals Tp of the individual pulses A to H fall short of the reciprocal value 1/f by a deviation Δ which is ⅛ of the reciprocal value 1/f. FIG. 6 (a) shows the pulses in the time space, whereas FIG. 6 (b) depicts the pulses A to H in the phase space, where they also raster scan the full phase space of $2\pi$ at the dominant frequency exactly once at intervals $I_P$ of $\pi/4$, but in a direction opposite to the pulses A to H according to FIG. 5 (b).

Figure 7:
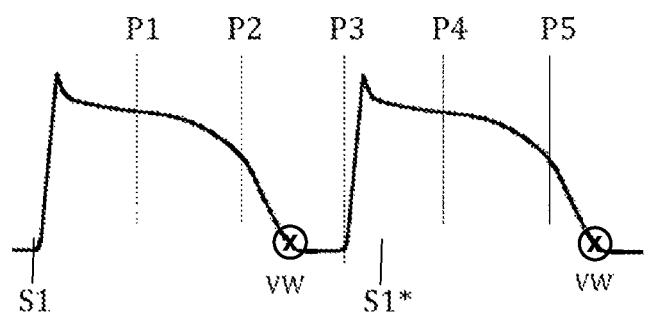
FIG. 7 illustrates a concept of suppressing atrial fibrillation (AF) without shock-induction of ventricular fibrillation (VF)

FIG. 7 schematically shows a procedure used to synchronize far-field anti-fibrillation pacing (FF-AFP) with ventricular activity, represented by a ventricular action potential. Using the ARI ("x") measured during ventricular pacing for 10 beats at a constant cycle length (S1S1=400 ms), the vulnerable window (VW) is defined, where VWmin=ARI−20 ms and VWmax=ARI+20 ms. The timing for the 5 FF-AFP pulses (P1-P5) is calculated for a constant P-P interval (e.g., 90 ms) so that P2 is delivered 10 ms before VWmin and P3 is delivered at least 10 ms after VWmax. P3 pre-empts the following S1 (S1*), and the next two pulses (P4 and P5) fall within the absolute refractory period of the ventricle.

Many variations and modifications may be made to the preferred embodiments of the invention without departing substantially from the spirit and principles of the invention. All such modifications and variations are intended to be included herein within the scope of the present invention, as defined by the following claims.

The invention claimed is:

1. An apparatus for terminating a high frequency arrhythmic electric state of a biological tissue, the apparatus comprising:
   at least one sensor for providing an electric signal representative of the present electric state of the biological tissue;
   a determination unit
      which determines from the electric signal at least one dominant frequency of the present electric state of the biological tissue, and
      which determines from the at least one dominant frequency whether the present electric state of the biological tissue is a high frequency arrhythmic electric state;
   an electric pulse generator for generating at least one series of electric pulses at intervals depending on the at least one dominant frequency; and
   at least one electrode connected to the pulse generator for applying the electric pulses to the biological tissue;
   wherein the determination unit, for terminating a determined high frequency arrhythmic electric state of the biological tissue,
   determines from the electric signal a dominance level indicative of how dominant the at least one dominant frequency is in the high frequency arrhythmic electric state; and
   triggers the electric pulse generator to generate the at least one series of electric pulses starting at a point in time at which the dominance level exceeds a predefined threshold value.

2. The apparatus of claim 1, wherein the threshold value is adjustable.

3. The apparatus of claim 1, wherein the threshold value is a percentage of a previously recorded maximum value of the dominance level.

4. The apparatus of claim 3, wherein the percentage is adjustable.

5. The apparatus of claim 1, wherein, for determining the dominance level, the determination unit filters the electric signal for frequency components in a frequency range extending on at least one side of the dominant frequency.

6. The apparatus of claim 1, wherein, for determining the dominance level, the determination unit compares the intensity of the electric signal at the dominant frequency with the intensity of the electric signal at least one neighboring frequency.

7. The apparatus of claim 1, wherein, in a set up mode which is only to be activated when the present electric state of the biological tissue is neither a high frequency arrhythmic electric state nor any other electrically exited state,
the at least one electrode applies the individual electric pulses to the biological tissue; and
the determination unit determines from the electric signals provided by the at least one sensor in response to the individual electric pulses a minimum suitable voltage of the electric pulses of the at least one series of electric pulses to be generated by the electric pulse generator for successfully terminating a future high frequency arrhythmic electric state of the biological tissue.

8. The apparatus of claim 7, wherein, in the set up mode, the electric pulse generator generates the individual electric pulses at the same duration in a range from 2 to 25 ms and at the different voltages in a range from 0.05 to 3 V/cm.

9. The apparatus of claim 1, wherein the electric pulse generator generates the electric pulses of the at least one series of electric pulses at such intervals and in such a number that the electric pulses raster scan a phase space defined by the at least one dominant frequency once.

10. The apparatus of claim 9, wherein the electric pulse generator generates the electric pulses of the at least one series of electric pulses at such time intervals that the electric pulses raster scan the phase space defined by the at least one dominant frequency at phase intervals in a range from $\pi/16$ to $2\pi/5$, preferably from $\pi/5$ to $2\pi/7$.

11. The apparatus of claim 10, wherein the electric pulse generator generates the electric pulses of the at least one series of electric pulses at time intervals deviating from the reciprocal value of the at least one dominant frequency by a deviation in time in a range from 1/32 to 1/5, preferably from 1/10 to 1/7, of the reciprocal value of the at least one dominant frequency.

12. The apparatus of claim 11, wherein the electric pulse generator generates the electric pulses of the at least one series of electric pulses at intervals exceeding the reciprocal value.

13. The apparatus of claim 1, wherein the electric pulse generator generates the electric pulses of the at least one series of electric pulses at a duration per pulse in a range from 2 to 25 ms, preferably from 5 to 15 ms.

14. The apparatus of claim 1, wherein the electric pulse generator generates the electric pulses of the at least one series of electric pulses at such a voltage that each electric pulse creates an electric field across the biological tissue in a range from 0.05 to 3 V/cm, preferably from 0.1 to 1 V/cm.

15. The apparatus of claim 1, wherein the electric pulse generator generates the electric pulses of the at least one series of electric pulses at an electric energy per pulse in a range from 1/400 to 1/2, preferably from 1/200 to 1/5, and even more preferably from 1/100 to 1/10, of a standard heart defibrillation energy.

16. The apparatus of claim 1, wherein the electric pulse generator generates a plurality of series of electric pulses, the electric pulses of each series of electric pulses raster scanning the full phase space defined by the same at least one dominant frequency once, and the single series of electric pulses of the plurality of series being applied to different electrodes connected to the electric pulse generator to successively create electric fields across the biological tissue in different spatial directions.

17. The apparatus of claim 1, wherein, after the electric pulse generator generated any series of electric pulses, the determination unit determines from the electric signal whether the biological tissue is still in the arrhythmic electric state, and wherein the electric pulse generator only generates any further series of electric pulses, if the biological tissue is still in the arrhythmic electric state.

18. The apparatus of claim 17, wherein the electric pulse generator generates at least one further series of electric pulses at a higher voltage than a previous series of electric pulses.

19. The apparatus of claim 17, wherein, if the determination unit, after a predefined number of series of electric pulses, determines that the biological tissue is still in the arrhythmic electric state, the electric pulse generator generates a single electric pulse of a standard heart defibrillation energy and; the at least one electrode applies the single electric pulses to the biological tissue.

20. The apparatus of claim 1, wherein the determination unit, in determining from the at least one dominant frequency whether the biological tissue is in a high frequency arrhythmic electric state, determines from the electric signal whether a dominant frequency of the present electric state of the biological tissue is in a frequency range from 5 to 20 Hz.

21. The apparatus of claim 1, wherein the determination unit determines the at least one dominant frequency of the present electric state of the biological tissue as the highest dominant frequency of the electric signal.

22. The apparatus of claim 1, wherein at least a part of a housing of the apparatus including the determination unit and the electric pulse generator forms a counter electrode connected to the pulse generator for applying the electric pulses to the biological tissue.

23. The apparatus of claim 1, wherein the at least one electrode connected to the pulse generator is a cardiac electrode.

24. The apparatus of claim 23, wherein the at least one electrode connected to the pulse generator is an intrathoracic electrode.

25. The apparatus of claim 1, wherein the at least one electrode connected to the pulse generator is a brain electrode.

26. The apparatus of claim 25, wherein the at least one electrode connected to the pulse generator is a non-intracerebral electrode.

27. The apparatus of claim 1, wherein the at least one electrode connected to the pulse generator is a skeletal muscle electrode.

28. The apparatus of claim 25, wherein the at least one electrode connected to the pulse generator is a non-subcutaneous electrode.

29. The apparatus of claim 1, wherein the at least one sensor is configured to provide an electric signal representative of the present electric state of an atrium of a heart, wherein the electrode connected to the pulse generator is configured to apply the electric pulses to the atrium, and wherein the apparatus further comprises:
at least one further sensor configured to provide a further electric signal representative of an ventricular action potential of a ventricle of the heart;
a further electric pulse generator configured to generate electric pacing pulses;
at least one further electrode connected to the further pulse generator and configured to apply the electric pacing pulses to the ventricle; and
a synchronization unit configured to synchronize the at least one series of electric pulses with the electric pacing pulses such that no electric pulse of the at least one series of electric pulses is applied in a vulnerable window during which the ventricle is susceptible to shock-induced ventricular fibrillation.

30. An apparatus for terminating an atrial fibrillation of an atrium of a heart, the apparatus comprising:
- at least one sensor configured to provide an electric signal representative of the present electric state of the atrium;
- a determination unit configured to determine from the electrical signal whether the present electric state of the biological tissue is an atrial fibrillation;
- an electric pulse generator for generating at least one series of electric low energy anti-fibrillation pacing pulses at intervals depending on the electrical signal;
- at least one electrode connected to the pulse generator configured to apply the low energy anti-fibrillation pacing pulses to the atrium;
- at least one further sensor configured to provide a further electric signal representative of an ventricular action potential of a ventricle of the heart;
- a further electric pulse generator configured to generate electric pacing pulses;
- at least one further electrode connected to the further pulse generator and configured to apply the electric pacing pulses to the ventricle; and
- a synchronization unit configured to synchronize the at least one series of low energy anti-fibrillation pacing pulses with the electric pacing pulses such that no low energy anti-fibrillation pacing pulse of the at least one series of low energy anti-fibrillation pacing pulses is applied in a vulnerable window during which the ventricle is susceptible to shock-induced ventricular fibrillation.

31. The apparatus of claim 30, wherein the at least one further electrode and the at least one further sensor are combined in one indwelling pacing/sensing catheter configured to be placed in the ventricle.

32. A method of terminating a high frequency arrhythmic electric state of a biological tissue, the method comprising:
- obtaining an electric signal representative of the present electric state of the biological tissue;
- determining from the electric signal at least one dominant frequency of the present electric state of the biological tissue;
- determining from the at least one dominant frequency whether the present electric state of the biological tissue is a high frequency arrhythmic electric state;
- determining from the electric signal a dominance level indicative of how dominant the at least one dominant frequency is in the high frequency arrhythmic electric state;
- generating at least one series of electric pulses at intervals depending on the at least one dominant frequency; and
- applying the electric pulses to the biological tissue starting at a point in time at which the dominance level exceeds a predefined threshold value for the biological tissue being in a determined high frequency arrhythmic electric state.

33. The method of claim 32, wherein the threshold value is a percentage of a previously recorded maximum value of the dominance level.

34. The method of claim 32, wherein, in determining the dominance level, the electric signal is filtered for frequency components in a frequency range extending on at least one side of the dominant frequency.

35. The method of claim 32, wherein, in determining the dominance level, the intensity of the electric signal at the dominant frequency is compared with the intensity of the electric signal at least one neighboring frequency.

36. The method of claim 32, and further comprising a set up step carried out when the present electric state of the biological tissue is neither a high frequency arrhythmic electric state nor any other electrically exited state, the set up mode comprising:
- generating individual electric pulses of a same duration and of different voltages;
- applying the individual electric pulses to the biological tissue;
- sensing electric signals at the biological tissue in response to the individual electric pulses; and
- determining from the electric signals a minimum suitable voltage of the electric pulses of the at least one series of electric pulses to be generated by the electric pulse generator for successfully terminating a future high frequency arrhythmic electric state of the biological tissue.

37. The method of claim 36, wherein, in the set up step, the individual electric pulses are generated at a same duration in a range from 2 to 25 ms and at different voltages in a range from 0.05 to 3 V/cm.

38. The method of claim 32, wherein the at least one series of electric pulses is generated such as to raster scan a full phase space defined by the at least one dominant frequency once.

39. The method of claim 38, wherein the electric pulses of the at least one series of electric pulses are generated at such time intervals that the electric pulses raster scan the phase space defined by the at least one dominant frequency at phase intervals in a range from $\pi/16$ to $2\pi/5$, preferably from $\pi/5$ to $2\pi/7$.

40. The method of claim 39, wherein the electric pulses of the at least one series of electric pulses are generated at time intervals deviating from a reciprocal value of the at least one dominant frequency by a deviation in time in a range from 1/32 to 1/5, preferably from 1/10 to 1/7, of the reciprocal value of the at least one dominant frequency.

41. The method of claim 40, wherein the electric pulses of the at least one series of electric pulses are generated at time intervals exceeding the reciprocal value.

42. The method of claim 32, wherein the electric pulses of the at least one series of electric pulses are generated at a duration per pulse in a range from 2 to 25 ms, preferably from 5 to 15 ms.

43. The method of claim 32, wherein the electric pulses of the at least one series of electric pulses are generated at such a voltage that each electric pulse creates an electric field across the biological tissue in a range from 0.05 to 3 V/cm, preferably from 0.1 to 1 V/cm.

44. The method of claim 32, wherein the electric pulses of the at least one series of electric pulses are generated at an electric energy in a range from 1/400 to 1/2, preferably from 1/200 to 1/5, and even more preferably from 1/100 to 1/10, of a standard heart defibrillation energy.

45. The method of claim 32, wherein a plurality of series of electric pulses are generated, the electric pulses of each series of electric pulses raster scanning the phase space defined by the same at least one dominant frequency, and wherein the single series of electric pulses of the plurality of series are applied to different electrodes to successively create electric fields across the biological tissue in different spatial directions.

46. The method of claim 32, and comprising, after generating any series of electric pulses, determining from the electric signal whether the biological tissue is still in the arrhythmic electric state, and only generating any further series of electric pulses, if the biological tissue is still in the arrhythmic electric state.

47. The method of claim 46, wherein any further series of electric pulses is generated at a higher voltage than the previous series of electric pulses.

48. The method of claim 46, wherein, if the biological tissue is still in the arrhythmic electric state after a predefined number of series of electric pulses, is generated at a higher voltage than the previous series of electric pulses, a single electric pulse of a standard heart defibrillation energy is generated and applied to the biological tissue.

49. The method of claim 32, and comprising, in determining from the at least one dominant frequency whether the biological tissue is in a high frequency arrhythmic electric state, determining from the electric signal whether a dominant frequency of the present electric state of the biological tissue is in a frequency range from 5 to 20 Hz.

50. The method of claim 32, and comprising, in determining the at least one dominant frequency of the present electric state of the biological tissue, determining the at least one dominant frequency as the highest dominant frequency of the electric signal.

51. The method of claim 32, wherein the electric pulses are applied to the biological tissue via at least one electrode and a counter electrode.

52. The method of claim 51, wherein the at least one electrode is a cardiac electrode which is placed via a cardiac catheter.

53. The method of claim 51, wherein the at least one electrode is a brain electrode which is placed extracranially.

54. The method of claim 51, wherein the at least one electrode is a skeletal muscle electrode which is placed non subcutaneously.

55. The method of claim 32, wherein the biological tissue is in an atrium of a heart, and wherein the method further comprises:
obtaining a further electric signal representative of an ventricular action potential of a ventricle of the heart;
generating electric pacing pulses;
applying the electric pacing pulses to the ventricle; and
synchronizing the at least one series of electric pulses with the electric pacing pulses such that no electric pulse of the at least one series of electric pulses is applied in a vulnerable window during which the ventricle is susceptible to shock-induced ventricular fibrillation.

56. A method of terminating an atrial fibrillation of an atrium of a heart, the method comprising:
obtaining an electric signal representative of the present electric state of the atrium;
determining from the electric signal whether the present electric state of the biological tissue is an atrial fibrillation;
generating at least one series of electric low energy anti-fibrillation pacing pulses at intervals depending on the electric signal;
obtaining a further electric signal representative of an ventricular action potential of a ventricle of the heart;
generating electric pacing pulses;
applying the electric pacing pulses to the ventricle;
generating at least one series of electric low energy anti-fibrillation pacing pulses at intervals depending on the electric signal;
applying the low energy anti-fibrillation pacing pulses to the atrium; and
synchronizing the at least one series of low energy anti-fibrillation pacing pulses with the electric pacing pulses such that no low energy anti-fibrillation pacing pulse of the at least one series of low energy anti-fibrillation pacing pulses is applied in a vulnerable window during which the ventricle is susceptible to shock-induced ventricular fibrillation.

* * * * *